(12) United States Patent
Masubuchi

(10) Patent No.: US 9,925,073 B2
(45) Date of Patent: Mar. 27, 2018

(54) STENT

(71) Applicant: TERUMO KABUSHIKI KAISHA, Shibuya-ku, Tokyo (JP)

(72) Inventor: Yuki Masubuchi, Hiratsuka (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 194 days.

(21) Appl. No.: 14/873,042

(22) Filed: Oct. 1, 2015

(65) Prior Publication Data

US 2016/0022446 A1 Jan. 28, 2016

Related U.S. Application Data

(63) Continuation of application No. PCT/JP2013/059822, filed on Apr. 1, 2013.

(51) Int. Cl.
| | |
|---|---|
| *A61F 2/06* | (2013.01) |
| *A61F 2/844* | (2013.01) |
| *A61F 2/915* | (2013.01) |
| *A61F 2/966* | (2013.01) |
| *A61F 2/95* | (2013.01) |

(52) U.S. Cl.
CPC ............ *A61F 2/844* (2013.01); *A61F 2/915* (2013.01); *A61F 2/95* (2013.01); *A61F 2/966* (2013.01); *A61F 2002/91583* (2013.01); *A61F 2002/9505* (2013.01); *A61F 2002/9534* (2013.01); *A61F 2002/9665* (2013.01)

(58) Field of Classification Search
CPC .. A61F 2/844; A61F 2/915; A61F 2/95; A61F 2/966; A61F 2002/9505; A61F 2002/9511; A61F 2002/9528; A61F 2002/9534; A61F 2002/9665
See application file for complete search history.

(56) References Cited

U.S. PATENT DOCUMENTS

| | | | |
|---|---|---|---|
| 8,080,053 B2 * | 12/2011 | Satasiya | ................... A61F 2/91 623/1.15 |
| 2006/0020321 A1 | 1/2006 | Parker | |
| 2008/0021544 A1 | 1/2008 | Majereak et al. | |
| 2008/0114442 A1 | 5/2008 | Mitchell et al. | |

FOREIGN PATENT DOCUMENTS

| | | |
|---|---|---|
| JP | 2008-29839 | 2/2008 |
| JP | 2008-507376 A | 3/2008 |
| JP | 2008-119481 | 5/2008 |
| JP | 4923187 B2 | 4/2012 |

OTHER PUBLICATIONS

International Search Report (PCT/ISA/210) dated Jul. 2, 2015, by the Japanese Patent Office as the International Searching Authority for International Application No. PCT/JP2013/059822.

* cited by examiner

*Primary Examiner* — Ashley Fishback

(74) *Attorney, Agent, or Firm* — Buchanan Ingersoll & Rooney PC

(57) ABSTRACT

A stent is disclosed, which is formed in a cylindrical shape and has a cavity portion, and is freely switched between an expanded state and a contracted state where the stent contracts to a central axis (O) side from the expanded state. The stent has an anchor portion which protrudes to a central axis (O) side relative to an inner surface surrounding the cavity portion in the contracted state, and which is displaced to the inner surface side in the expanded state relative to a protruded position in the contracted state.

19 Claims, 9 Drawing Sheets

STENT

CROSS-REFERENCES TO RELATED APPLICATIONS

This application is a continuation of International Application No. PCT/JP2013/059822 filed on Apr. 1, 2013, the entire content of which is incorporated herein by reference.

TECHNICAL FIELD

The present disclosure generally relates to a stent which is caused to indwell in a lesion in a living body lumen.

BACKGROUND DISCUSSION

In order to treat a lesion area appearing in a living body lumen such as blood vessels, biliary ducts, bronchial tubes, esophagi, and urethrae, stent treatment has been performed in which a stent is caused to indwell in the living body lumen by delivering the stent using a stent delivery device.

For example, JP-T-2008-507376 discloses a stent which is interposed between a sheath (cover) and a shaft (holder) in a contracted state of the sheath when the stent is delivered into the living body lumen, and which self-expands when the stent is exposed in a lesion by the sheath moving rearward. A rivet is attached to an end portion of the stent so that the stent does not follow the rearward movement of the sheath when the stent is exposed. The rivet is attached so as to protrude relative to an inner surface and an outer surface of the stent, and is locked by a ridge portion of the shaft. In this manner, a restriction (position stopping) on the stent moving along the shaft is imposed.

Incidentally, since the rivet protrudes beyond the inner side of the stent, interference with the flow of a body fluid after the stent indwells in the living body lumen can occur. For this reason, it can be desirable to set a protruded amount of the rivet to be as little as possible. However, in this case, the rivet is easily unlocked by the ridge portion, thereby leading to a disadvantage in that the stent is forced to follow the movement of the sheath.

In addition, although not disclosed in JP-T-2008-507376, the above-stent is exposed, thereby causing a possibility of poor indwelling of the stent. Accordingly, in a case of the stent treatment, if the stent is misaligned when exposed, the sheath is switched from the rearward movement to the forward movement so as to perform an operation for returning the stent into the sheath again. Therefore, it is desirable to adopt a configuration in which the stent does not follow bidirectional (rearward and forward) movement of the sheath.

SUMMARY

A stent is disclosed, which can more reliably prevent the stent from following the movement of a sheath, and which can help suppress an influence from a body fluid in a state where the stent indwells in a living body lumen.

A stent is disclosed, which is formed in a cylindrical shape and which has a cavity portion. The stent can be freely switched between an expanded state and a contracted state where the stent contracts to a central axis side from the expanded state. The stent can include a movable protruded portion which is protruded to the central axis side relative to an inner surface surrounding the cavity portion in the contracted state, and which is displaced to the inner surface side in the expanded state relative to a protruded position in the contracted state.

According to the above-described configuration, the stent has the movable protruded portion which is protruded to the central axis side relative to the inner surface surrounding the cavity portion in the contracted state. Accordingly, the movable protruded portion can be firmly locked by a ridge portion of an inner structure body which is accommodated in a lumen of a sheath, for example. Therefore, improved restriction force is given to the stent moving on the inner structure body, and thus, the stent can be prevented from following the movement of the sheath. As a result, an operator can accurately expand the stent inside a living body lumen, and thus, the stent can be satisfactorily indwelled at a desired position.

In addition, the movable protruded portion in the expanded state is displaced to the inner surface side relative to the protruded position in the contracted state. Accordingly, the stent is prevented from receiving an influence from a body fluid flowing in the living body lumen. For example, the stent is allowed to stably maintain an indwelling state inside the living body lumen. In addition, obstruction of flow of the body fluid can be minimized.

In accordance with an exemplary embodiment, it can be preferable to adopt a configuration in which the stent in the contracted state is accommodated in a lumen of a sheath which can be delivered into a living body lumen, and is arranged so as to surround an inner structure body which is inserted into the lumen, and in which the movable protruded portion inclines in a direction in which the sheath is movable relative to the inner structure body, and a peak portion of the movable protruded portion protruded inward most relative to the inner surface can be locked by a locking portion formed on an outer peripheral surface of the inner structure body.

In accordance with an exemplary embodiment, the movable protruded portion inclines in the direction in which the sheath is movable. Accordingly, the stent enables the movable protruded portion to abut on and press the locking portion of the inner structure body. Accordingly, the stent can be reliably prevented from following the movement of the sheath.

In addition, the stent may include an element wire configuring a stent body and an element wire configuring the movable protruded portion, and the element wire configuring the movable protruded portion may be formed of a shape memory alloy.

In accordance with an exemplary embodiment, the element wire configuring the movable protruded portion is formed of the shape memory alloy. Accordingly, the movable protruded portion can easily protrude to the central axis side in the contracted state of the stent. In addition, in the expanded state of the stent, the movable protruded portion can be smoothly and elastically restored together with the element wire configuring the stent body, and can be displaced to the inner surface side.

Furthermore, for example, preferably, the element wire configuring the movable protruded portion is more flexible than the element wire configuring the stent body.

In accordance with an exemplary embodiment, the element wire configuring the movable protruded portion can be flexible. Accordingly, in the contracted state of the element wire configuring the stent, the movable protruded portion can protrude to the central axis side after being actively and elastically deformed.

In accordance with an exemplary embodiment, the element wire configuring the stent body may have a pair of extension portions which extend toward an axial end portion of the stent and a turn-up peak portion which is curvedly connected to the pair of extension portions. The element wire configuring the movable protruded portion in the expanded state may be connected to the pair of extension portions so as to incline in a protruded direction in the contracted state.

In accordance with an exemplary embodiment, the movable protruded portion in the expanded state inclines in the protruded direction in the contracted state. Accordingly, when the stent is switched from the expanded state to the contracted state (when the stent is elastically deformed), the movable protruded portion can easily protrude to the central axis side.

In addition, the element wire configuring the movable protruded portion in the expanded state may have a valley portion on a side opposite to the protruded direction.

In accordance with an exemplary embodiment, the movable protruded portion has the valley portion on the side opposite to the protruded direction. Accordingly, when the stent is elastically deformed, the stent can be operated so as to fold the valley portion, and thus the movable protruded portion can more reliably protrude to the central axis side.

Furthermore, both end portions of the movable protruded portion may be respectively connected to two connection points on the pair of extension portions. For example, preferably, a length extending along the element wire configuring the movable protruded portion between the two connection points is shorter than a length extending along the element wire configuring the stent body between the two connection points.

In accordance with an exemplary embodiment, the length extending along the element wire configuring the movable protruded portion between the two connection points is shorter than the length extending along the element wire configuring the stent body. Accordingly, in the expanded state of the stent, the movable protruded portion can be moved sufficiently close to the inner surface side of the stent, and thus it is possible to further minimize a possibility that the movable protruded portion may receive the flow of the body fluid.

In accordance with an exemplary embodiment, a stent is disclosed comprising: a cylindrical shape having a cavity portion, the stent being configured to be freely switched between an expanded state and a contracted state where the stent contracts to a central axis (O) side from the expanded state; and a movable protruded portion which is protruded to the central axis (O) side relative to an inner surface surrounding the cavity portion in the contracted state, and which is displaced to the inner surface side in the expanded state relative to a protruded position in the contracted state.

DETAILED DESCRIPTION

Hereinafter, preferred exemplary embodiments of a stent according to the present disclosure will be described in detail with reference to the accompanying drawings.

The stent is caused to indwell in a living body lumen in order to treat a lesion appearing in the living body lumen such as blood vessels, biliary ducts, bronchial tubes, esophagi, urethrae, and the like by using interventional procedure into the living body lumen (procedure for causing a device for accommodating the stent to delivering the stent into the living body lumen). In particular, description will be made in detail with regard to the stent according to the present embodiment which is caused to indwell in stenosis (lesion area) appearing in the blood vessel so as to expand and support the stenosis.

Figure 1:
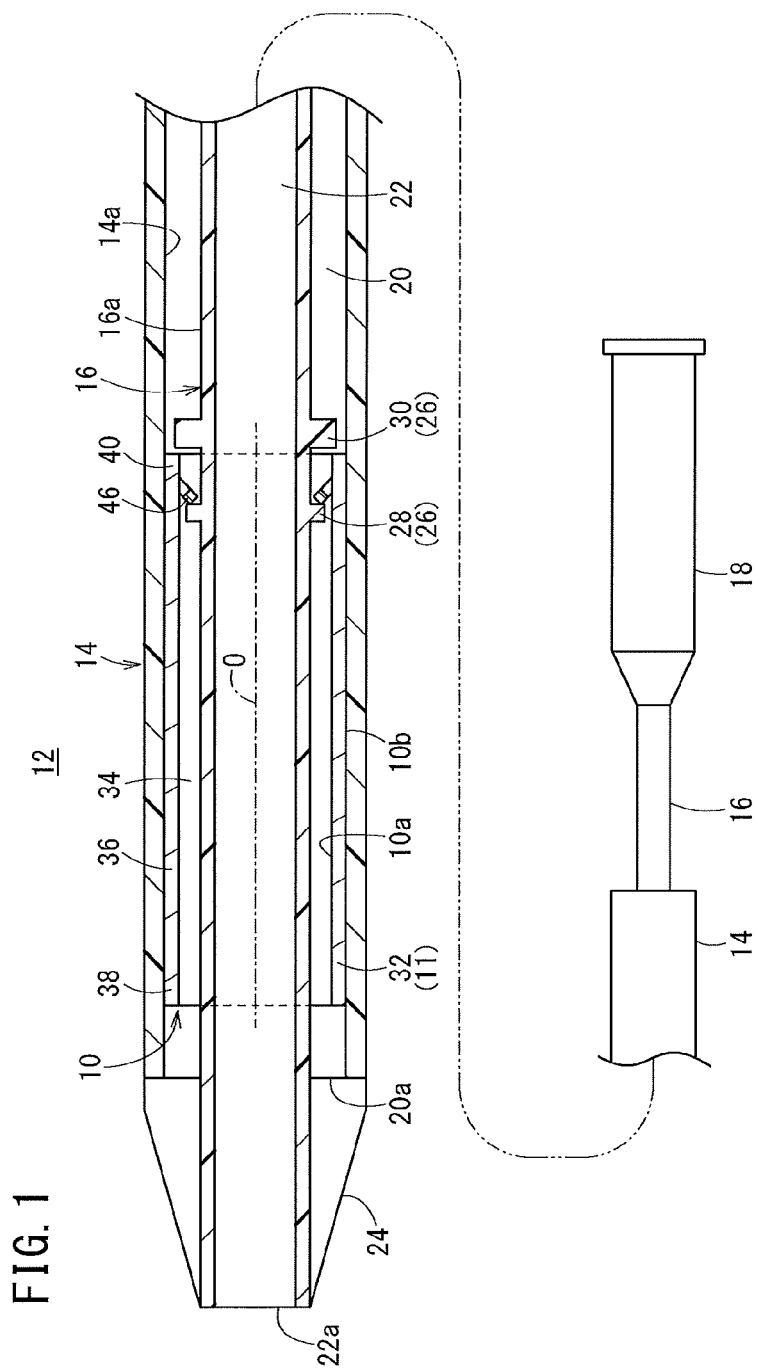
FIG. 1 is a partial side sectional view illustrating a stent and a device for accommodating the stent according to an exemplary embodiment of the present disclosure.

As illustrated in FIG. 1, a stent 10 is accommodated in a distal side of a device 12 (catheter) for delivering the stent, and is delivered to the stenosis inside the blood vessel. The device 12 can include a sheath 14 which has a length so as to be able to reach the stenosis, a shaft 16 which is inserted into the sheath 14 and in which the stent 10 is placed on an outer peripheral surface thereof, and an operation unit 18 which is connected to a proximal portion of the shaft 16 so as to operate the device 12.

The sheath 14 is a flexible tubular body which is inserted and delivered into the blood vessel, and has an accommodating lumen 20 (lumen) which is formed so as to penetrate in an axial direction (longitudinal direction). The accommodating lumen 20 is configured so that an inner wall 14a of the sheath 14 surrounds the periphery with a substantially constant inner diameter, and the shaft 16 is arranged in the sheath 14 so as to be movable forward and rearward. In addition, a distal opening 20a communicating with the accommodating lumen 20 is formed on a distal surface of the sheath 14, and a distal portion of the shaft 16 is exposed from the distal opening 20a.

The shaft 16 is formed so as to be longer than an axial length (entire length) of the sheath 14, and is exposed from both ends in the axial direction of the sheath 14. The stent 10 is placed on the distal side of the shaft 16 so as to surround an outer wall 16a of the shaft 16. The stent 10 is accommodated in the accommodating lumen 20 by being interposed between the inner wall 14a of the sheath 14 and the outer wall 16a of the shaft 16.

In addition, a guidewire lumen 22 is formed inside the shaft 16 so as to penetrate along the axial direction. A guidewire (not illustrated) which is delivered into the blood vessel in advance is inserted into the guidewire lumen 22. The device 12 is inserted and delivered into the blood vessel along the guidewire.

Furthermore, a nose cone 24 which tapers in a direction toward the distal end can be disposed in the distal portion of the shaft 16. The shaft 16 penetrates a central portion of the nose cone 24, and a wire outlet 22a communicating with the guidewire lumen 22 is formed on a distal surface of the nose cone 24. A proximal surface of the nose cone 24 is formed in a flat shape, and can come into contact with a distal surface of the sheath 14 in a liquid-tight manner. Therefore, the distal opening 20a of the accommodating lumen 20 can be closed when delivered into the blood vessel, thereby preventing blood from flowing into the accommodating lumen 20.

In the shaft 16, a position relatively close to the proximal surface of the nose cone 24 serves as a placement portion of the stent 10. A stent locking portion 26 for helping prevent the stent 10 from following the forward and rearward movement of the sheath 14 (misalignment in the axial direction of the stent 10) is disposed on the outer wall 16a of the placement portion. The stent locking portion 26 is configured to include a first ridge portion 28 and a second ridge portion 30 which are formed in an annular shape along a circumferential direction of the outer wall 16a of the shaft 16. The first ridge portion 28 is disposed on the further distal side relative to the second ridge portion 30, and engages with an anchor portion 46 of the stent 10 (to be described later). The second ridge portion 30 protrudes radially outward relative to the first ridge portion 28, and faces a proximal end (turn-up peak portion 40b) of the stent 10. When the sheath 14 is operated so as to move rearward, the second ridge portion 30 is brought into contact with the proximal end of the stent 10, thereby helping prevent the stent 10 from following the sheath 14 (moving rearward).

The stent 10 can include a stent body 11 having a self-expandable function, and is accommodated inside the sheath 14 (accommodating lumen 20) in a state where the stent 10 is folded so as to restrict the expansion (contracted state). The stent 10 automatically expands when the sheath 14 moves rearward relative to the shaft 16 and is exposed from the sheath 14, and is changed to the expanded state which can support the stenosis.

Figure 2:
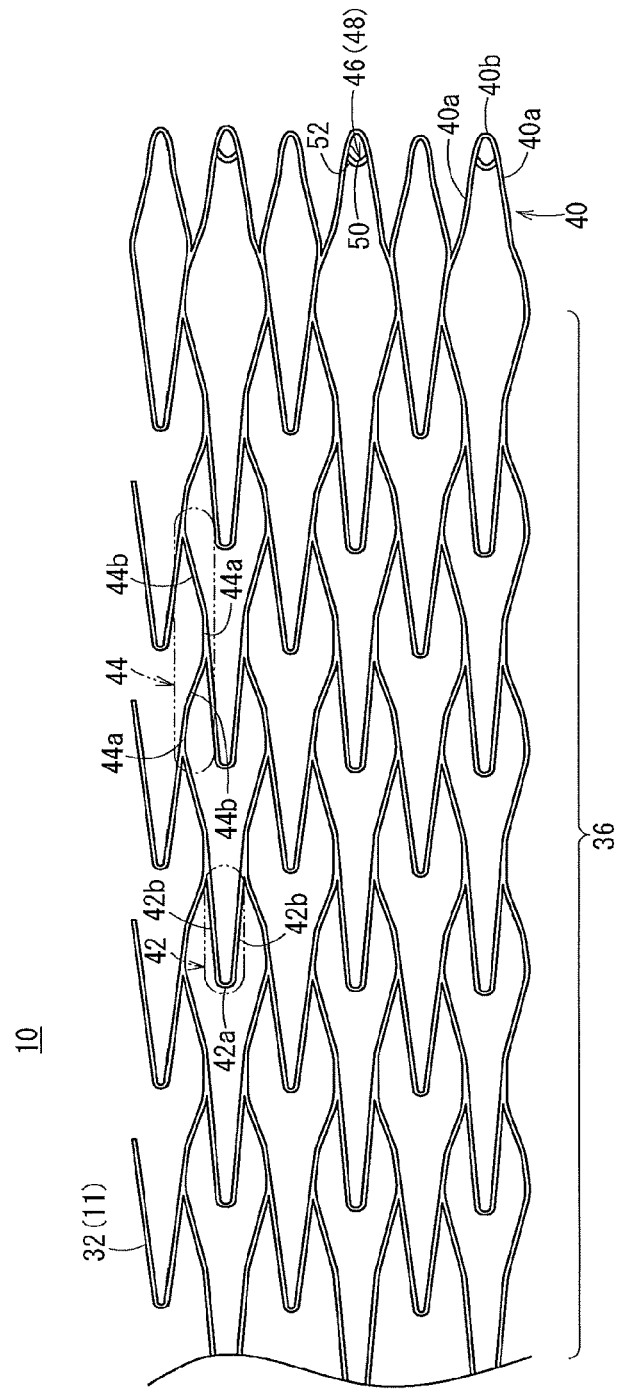
FIG. 2 is a partial plan view illustrating the stent in FIG. 1 in a contracted stated.
Figure 3:
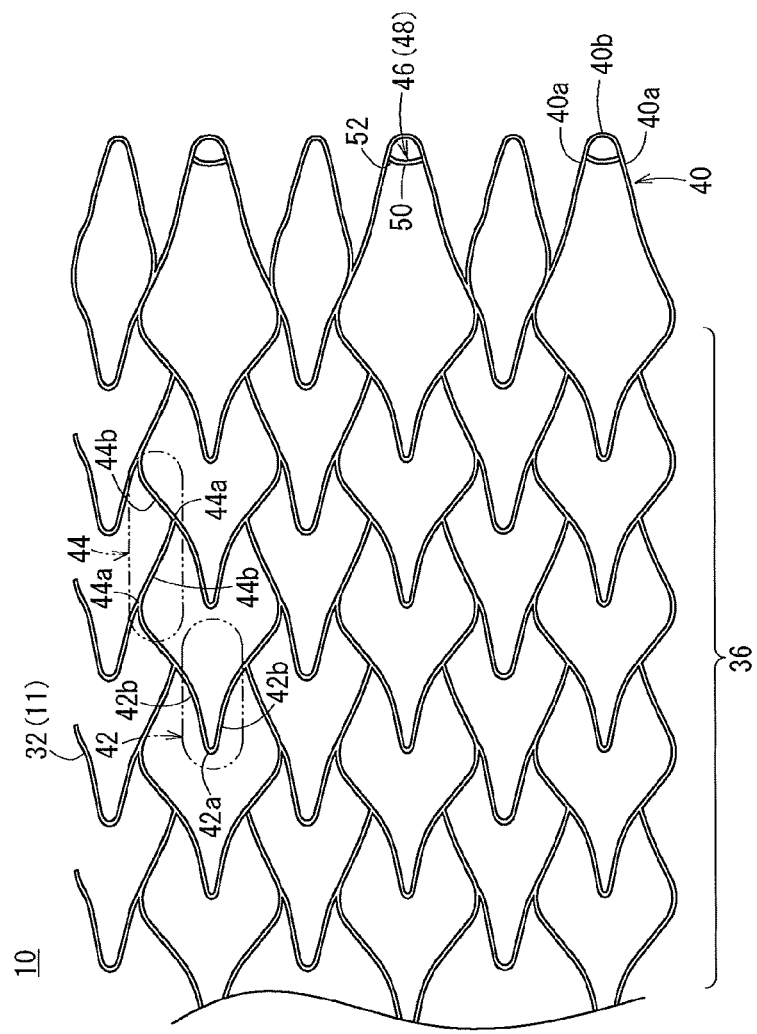
FIG. 3 is a partial plan view illustrating of the stent in FIG. 1 in an expanded state.

As illustrated in FIGS. 2 and 3, the stent body 11 can include stent strut 32 (element wire) whose shape is memorized so as to exhibit a predetermined shape. That is, the stent struts 32 are connected to one another in the circumferential direction so as to configure a mesh shape, thereby forming the stent body 11 having a cylindrical shape. In this manner, the stent 10 is allowed to have a cavity portion 34 (refer to FIG. 1) penetrating in the axial direction. The shaft 16 is inserted into the cavity portion 34 when the stent 10 is accommodated in the device 12.

In accordance with an exemplary embodiment, the stent strut 32 can include a suitable material having self-expandable elastic force (for example, superelasticity) when exposed from the sheath 14. For example, a configuration material of the stent strut 32 can include various metal materials such as stainless steel, Ni—Ti alloys, Cu—Zn alloys, Ni—Al alloys, Co—Cr alloys, tungsten, tungsten alloys, titanium, titanium alloys, tantalum, relatively rigid polymeric materials such as polyamide, polyimide, ultra-high molecular weight polyethylene, polypropylene, fluorine resin, and a proper combination of these materials.

The stent body 11 can include a cylindrical body portion 36 which has a larger outer diameter than an inner diameter of a blood vessel 100 (refer to FIG. 7A) where the stent body 11 indwells in a natural state, and which has a longer axial length than an appearing range of stenosis 102 (refer to FIG. 7A), a distal turn-up portion 38 (refer to FIG. 1) which is connected to the distal side of the cylindrical body portion 36, and a proximal turn-up portion 40 which is connected to the proximal side of the cylindrical body portion 36. The distal turn-up portion 38 is formed in a shape symmetrical to the proximal turn-up portion 40 (however, does not include the anchor portion 46). Therefore, in the following description, the proximal turn-up portion 40 will be representatively described, and description of the distal turn-up portion 38 will be omitted.

The cylindrical body portion 36 in the contracted state is elastically deformed so as to contract radially inward and to extend in the axial direction. Since the stent strut 32 is curvedly formed, the cylindrical body portion 36 has a V-shaped frame portion 42 and a wavy frame portion 44 which are formed in different shapes. The V-shaped frame portion 42 and the wavy frame portion 44 are arrayed side by side at multiple locations along the axial direction, and are alternately arranged along the circumferential direction. For example, the cylindrical body portion 36 is formed in a cylindrical shape in which a row of the V-shaped frame portion 42 and a row of the wavy frame portion 44 are alternately disposed in the circumferential direction.

One V-shaped frame portion 42 has a V-shaped peak portion 42a and a pair of V-shaped extension portions 42b connected to the V-shaped peak portion 42a. One wavy frame portion 44 has a wavy peak portion 44a which includes amplitude along the circumferential direction of the cylindrical body portion 36 and a wavy extension portion 44b which curvedly connects the wavy peak portions 44a to each other. The pair of V-shaped extension portions 42b bridge between the V-shaped peak portion 42a and the wavy peak portion 44a. In this manner, the row of the V-shaped frame portion 42 and the row of the wavy frame portion 44 are connected to each other.

The proximal turn-up portion 40 connected to the cylindrical body portion 36 is disposed at multiple locations along the circumferential direction of the stent body 11 so as to face the V-shaped frame portion 42. The proximal turn-up portion 40 has a pair of proximal side extension portions 40a, which extend in the proximal direction from a connection portion with the wavy peak portion 44a, and a turn-up peak portion 40b which is curvedly connected to the pair of proximal side extension portions 40a. In accordance with an exemplary embodiment, the proximal turn-up portion 40 forms the proximal end of the stent 10 in such a way that the stent strut 32 extending from one wavy peak portion 44a is turned up in the turn-up peak portion 40b, and further forms a space surrounded by the stent strut 32 by extending the stent strut 32 toward the other corrugated peak portion 44a.

In the proximal turn-up portion 40, the pair of proximal side extension portions 40a are displaced so as to move close to each other in the contracted state (refer to FIG. 2). In this manner, the turn-up peak portion 40b is brought into a curved state having a large curvature. In addition, the pair of proximal side extension portions 40a are displaced so as to be away from each other in the expanded state (refer to FIG. 3). In this manner, the turn-up peak portion 40b is brought into a curved state having a small curvature.

Then, the stent 10 has a configuration in which the stent body 11 (proximal turn-up portion 40) is provided with the anchor portion 46 (movable protruded portion). As previously described, when the stent 10 is exposed, there is a possibility of expanding the stent 10 while the stent 10 is displaced from an indwelling target position (desired position). In this case, the operation of the sheath 14 is switched from the rearward movement to the forward movement so as to perform an operation for accommodating the stent 10 in the accommodating lumen 20 again. When the sheath 14 moves forward, the stent 10 is interfered with (receives friction force from) by the inner wall 14a of the sheath 14, and thus pressure (forward moving force) moving in the distal direction is applied to the stent 10. The anchor portion 46 helps prevent the stent 10 from moving along the shaft 16 by following the forward movement of the sheath 14. For example, the anchor portion 46 is disposed in order to maintain a position of the stent 10 placed on the shaft 16.

Figure 4:
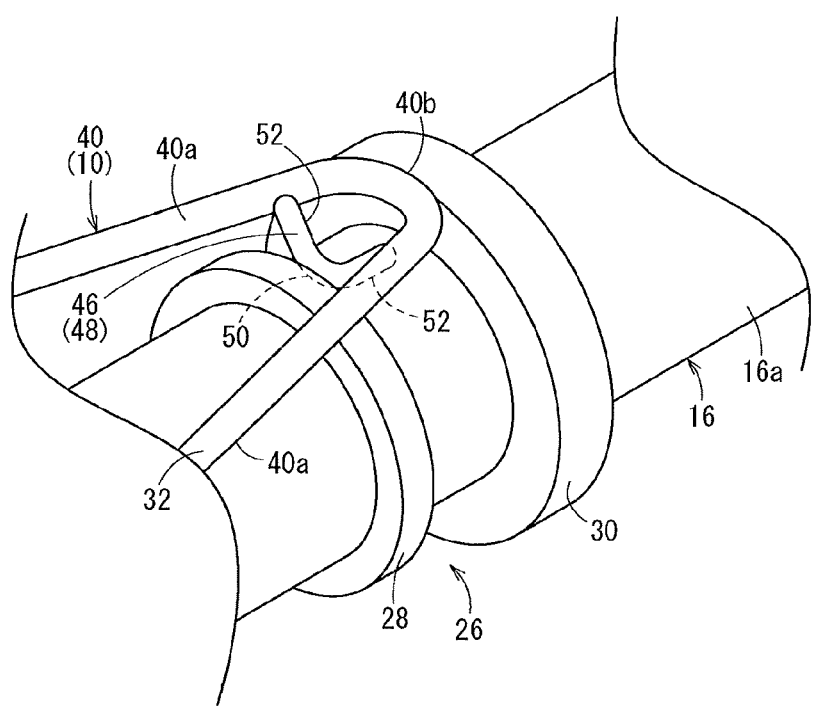
FIG. 4 is a partial perspective view illustrating an engagement state between an anchor portion and a stent locking portion in FIG. 1.

As illustrated in FIG. 4, in the contracted state of the stent 10, the anchor portion 46 protrudes (moves forward) to a central axis O (refer to FIG. 1) side of the stent 10 relative to the inner surface 10a configuring the cavity portion 34. In this manner, the anchor portion 46 can be locked by the first ridge portion 28 of the shaft 16. In this manner, even if the stent 10 is intended to move forward in the distal direction, the anchor portion 46 and the first ridge portion 28 engage with each other, thereby helping prevent the stent 10 from moving forward. In addition, the anchor portion 46 has a configuration in which the stent 10 is deployed inside the blood vessel and is brought into the expanded state so as to move rearward (to be retracted) to the inner surface 10a side of the stent 10 (also refer to FIG. 7C).

The anchor portion 46 is disposed at an intermediate position of the proximal side extension portion 40a of the proximal turn-up portion 40. The anchor portion 46 is configured to include an anchor strut 48 (element wire) which draws a substantially V-shape (alternatively, a substantially arc shape) as a whole so as to face a curved shape of the turn-up peak portion 40b. Both end portions of the anchor strut 48 are respectively connected to a pair of connection points C1 and C2 of the proximal side extension portion 40a. In accordance with an exemplary embodiment, a cell (closed cell) closed by the proximal turn-up portion 40 and the anchor portion 46 is formed in the proximal portion of the stent 10.

The anchor portion 46 is disposed at every other location of the proximal turn-up portions 40 arrayed side by side in the circumferential direction of the stent 10. In this manner, three anchor portions 46 are formed at substantially equal intervals (intervals of 120°) in the circumferential direction of the stent 10. The number of the anchor portions 46 disposed in the stent 10 is not particularly limited. However, for example, preferably, the stent 10 is configured to include two or more anchor portions 46, and the anchor portions 46 adjacent to each other are formed at positions having equal intervals. When the stent 10 has two or more anchor portions 46 in this way, the respective anchor portions 46 can be equally (without being unilaterally biased) locked by the first ridge portion 28 of the shaft 16. As a matter of course, only one anchor portion 46 may be disposed in the stent 10.

As illustrated in FIGS. 5A to 6C, the anchor portion 46 has a displacement peak portion 50 which faces the turn-up peak portion 40b of the proximal turn-up portion 40, and a pair of bridge portions 52 which extend from the displacement peak portion 50 to the pair of connection points C1 and C2. The displacement peak portion 50 is a portion which protrudes to a protruded position which is farthest away from the inner surface 10a (refer to FIG. 1) of the stent 10 in the contracted state, for example, the displacement peak portion 50 is most greatly displaced (protruded) portion in the anchor portion 46. The pair of bridge portions 52 are operation portions which elastically displace the displacement peak portion 50.

Figure 5A:
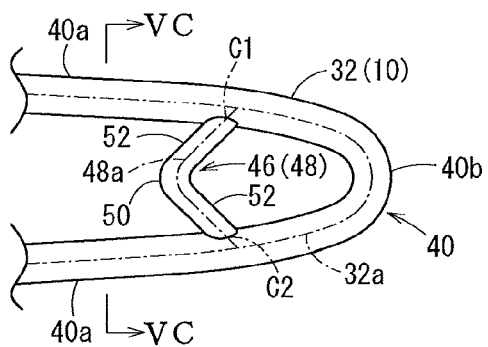
FIG. 5A is a plan view illustrating a part of both an anchor portion and a proximal turn-up portion in the contracted state.
Figure 5B:
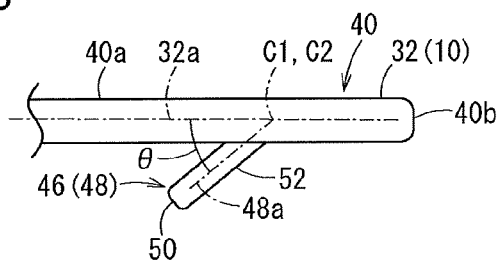
FIG. 5B is a side view of FIG. 5A.
Figure 5C:
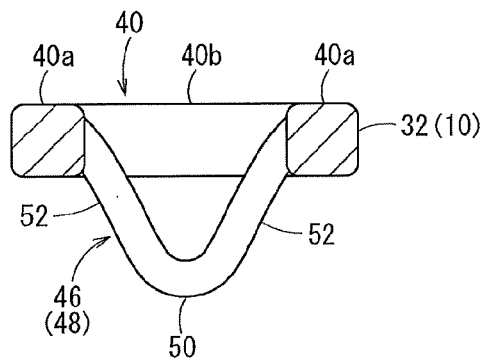
FIG. 5C is a sectional view taken along line VC-VC in FIG. 5A.
Figure 6A:
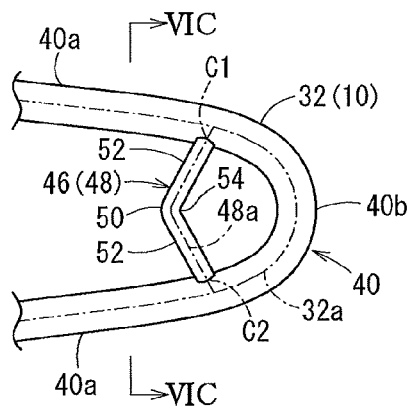
FIG. 6A is a plan view illustrating a part of both the anchor portion and the proximal turn-up portion in the expanded state.
Figure 6B:
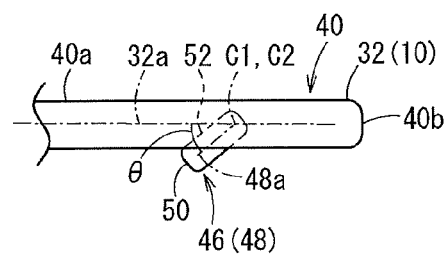
FIG. 6B is a side view of FIG. 6A.
Figure 6C:
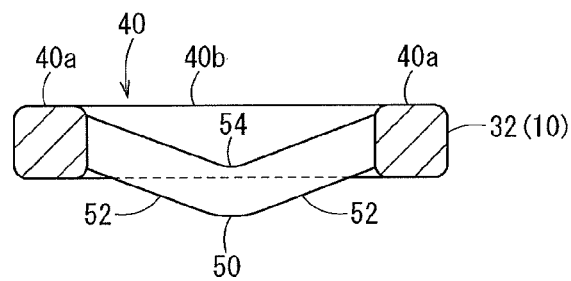
FIG. 6C is a sectional view taken along line VIC-VIC in FIG. 6A.

In accordance with an exemplary embodiment, in the expanded state of the stent 10 (proximal turn-up portion 40) illustrated in FIGS. 6A to 6C, the pair of proximal side extension portions 40a are separated from each other, and are operated so as to extend the pair of bridge portions 52 in the width direction (circumferential direction of the stent 10). In response to this operation, the displacement peak portion 50 is pulled to the inner surface 10a side of the stent 10. Then, in the contracted state of the stent 10 illustrated in FIGS. 5A to 5C, the pair of proximal side extension portions 40a move close to each other, and are operated so as to contract the pair of bridge portions 52 in the width direction (circumferential direction of the stent 10). In response to this operation, the displacement peak portion 50 is caused to protrude (move forward) to the central axis O side (lower side in FIG. 5C) of the stent 10. The displacement peak portion 50 comes into contact with the first ridge portion 28 of the shaft 16 at the protruded (forward moving) position, which helps enable the anchor portion 46 to be actually locked by the first ridge portion 28.

The anchor portion 46 is formed so that the axial length (dimension of the anchor portion 46) of the anchor strut 48 connecting the pair of connection points C1 and C2 is shorter than the axial length of the stent strut 32 connecting the pair of connection points C1 and C2 of the proximal turn-up portion 40. In this manner, the anchor portion 46 is spread out by the proximal turn-up portion 40 in the expanded state, thereby gradually showing a substantially V-shape. In accordance with an exemplary embodiment, the length extending along the anchor strut 48 between the pair of connection points C1 and C2 is shorter than the length extending along the stent strut 32 between the pair of connection points C1 and C2. Accordingly, in the expanded state of the stent 10, the anchor portion 46 can move sufficiently close to the inner surface 10a side of the stent 10.

In addition, as illustrated in FIG. 6B, the anchor portion 46 in the expanded state is configured to incline to the proximal turn-up portion 40 by a predetermined inclining angle θ. In accordance with an exemplary embodiment, the anchor portion 46 is connected to the stent 10 so that a second surface 48a configured to include the axis of the anchor strut 48 inclines to a first surface 32a configured to include the axis of the proximal turn-up portion 40 (stent strut 32). In this manner, as illustrated in FIG. 5B, even in the contracted state of the stent 10, the pair of bridge portions 52 protrude in the obliquely distal direction, thereby supporting the displacement peak portion 50.

In accordance with an exemplary embodiment, for example, it can be preferable to set the inclining angle θ of the second surface 48a of the anchor portion 46 with respect to the first surface 32a of the proximal turn-up portion 40 in the contracted state to fall within a range of 0<θ<45°. Since the inclining angle θ is set to fall within this range, the anchor portion 46 can directly transmit forward moving force applied to the stent 10 to the facing first ridge portion 28. Accordingly, a mutually locked state can be satisfactorily maintained.

In addition, a protruded amount of the anchor portion 46 (displacement peak portion 50) in the contracted state may be appropriately designed depending on a gap between the outer wall 16*a* of the shaft 16 and the inner surface 10*a* of the stent 10, a protruded height of the first ridge portion 28, a thickness of the stent strut 32, or the like. For example, when the stent strut 32 is 20 μm, it can be preferable that the anchor portion 46 protrudes by an amount of 10 μm or greater. In this manner, the anchor portion 46 can be sufficiently firmly locked by the first ridge portion 28.

A configuration material of the anchor portion 46 (anchor strut 48) is not particularly limited. For example, preferably, the materials included in the configuration material of the stent body 11 (stent strut 32) can be used. In particular, for example, a shape memory alloy can be used so that the anchor portion 46 can be easily elastically restored when the contracted state is switched to the expanded state. For example, it can be more preferable to configure the anchor portion 46 by using a Ti—Ni alloy containing Ni of 49 atomic % to 53 atomic % which shows superelasticity at living body temperature (approximately 37° C.). The stent strut 32 and the anchor strut 48 may be formed by using the same material (composition), or may be formed by using different materials.

The anchor strut 48 is formed so as to be thinner than the stent strut 32, and is more likely to be elastically deformed than the proximal turn-up portion 40. For example, in accordance with an exemplary embodiment, the anchor strut 48 can be more flexible than the stent strut 32. Accordingly, when the stent 10 is accommodated in the device 12, and when the stent 10 is switched from the expanded state to the contracted state, the anchor portion 46 is easily elastically deformed. In accordance with an exemplary embodiment, the bridge portion 52 is actively deformed with respect to the proximal turn-up portion 40 parallel to the central axis O of the stent 10, and the displacement peak portion 50 relatively easily protrudes (moves forward and is displaced) to the central axis O side relative to the inner surface 10*a*.

In addition, in the expanded state of the stent 10, for example, it can be preferable that a valley portion 54 (folded portion) is formed in a portion opposite to the protruded direction of the displacement peak portion 50. As illustrated in FIG. 6C, in a sectional view, the valley portion 54 is formed so as to incline to the inner surface 10*a* side while the pair of bridge portions 52 warp to the outer surface 10*b* side of the stent 10. In this manner, when the stent 10 is contracted, the valley portion 54 smoothly guides elastic deformation of the anchor portion 46 to the central axis O side.

A method of forming the anchor portion 46 is not particularly limited, and various processing methods can be employed. For example, when the anchor portion 46 is formed by using the same material as that of the stent body 11, removing process such as cutting, grinding, and the like may be carried out by using the same base material. When the anchor portion 46 is formed by using the different material from that of the stent body 11, bonding process for the stent body 11 by using welding caulking and the like may be carried out. In addition, in a case of the removing process or the bonding process, the anchor portion 46 is formed so as to be parallel to the proximal turn-up portion 40 of the stent body 11. In this manner, during the subsequent process, the anchor portion 46 may be processed into the above-described shape by exerting plastic deformation using heat setting, pressing or the like for the shape memory alloy.

The anchor portion 46 may be configured to have X-ray contrasting property different from that of the stent body 11. In this manner, a position of the anchor portion 46 can be confirmed by using X-ray radiography, thereby enabling stent treatment to be satisfactorily performed.

The stent 10 according to the present embodiment is basically configured as described above. Hereinafter, operational effects thereof will be described.

As illustrated in FIG. 1, before the stent treatment is performed, the stent 10 is accommodated together with the shaft 16 in the accommodating lumen 20 of the sheath 14. When accommodated, the stent 10 is elastically deformed and is brought into the contracted state by receiving pressing force from the inner wall 14*a* of the sheath 14. In addition, the stent 10 is placed on the distal side of the shaft 16 so that the anchor portion 46 is interposed between the first ridge portion 28 and the second ridge portion 30 of the shaft 16. Since the stent 10 is brought into the contracted state, the anchor portion 46 protrudes to the central axis O side relative to the inner surface 10*a* of the stent 10.

In the above-described state, an operator (surgeon or the like) grasps and operates the proximal side of the device 12, and delivers the distal portion of the device 12 toward the stenosis 102 inside the blood vessel 100 by using X-ray radiography. Then, at a stage where the distal portion of the device 12 reaches the stenosis 102, the stent 10 is deployed from the device 12.

Figure 7A:
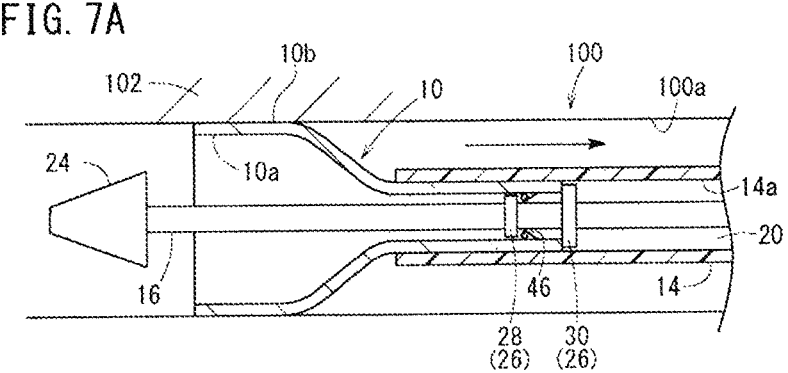
FIG. 7A is a first explanatory view for describing an operation when the stent in FIG. 1 expands.

As illustrated in FIG. 7A, when the stent 10 is deployed, the sheath 14 is moved rearward relative to the shaft 16, thereby exposing the stent 10 from the distal opening 20*a* of the sheath 14. When exposed from the sheath 14, the stent 10 automatically expands radially outward from the distal side thereof, and is switched to the expanded state. The expansion force of the stent 10 is applied to the outer surface 10*b* so as to spread out a vascular wall 100*a* of the blood vessel 100, and the stent 10 is fixed to the blood vessel 100. When the stent 10 is expanded, pressure (rearward moving force) acting from the inner wall 14*a* of the sheath 14 in the proximal direction is applied to the stent 10. In accordance with an exemplary embodiment, the turn-up peak portion 40*b* of the stent 10 comes into contact with the second ridge portion 30 so as to restrict the movement (displacement) of the stent 10. Accordingly, the stent 10 can be smoothly exposed from the sheath 14.

In addition, when the stent 10 is exposed (when the sheath 14 is operated to move rearward), an operator confirms a position of the distal portion of the device 12 and the stenosis 102 by using X-ray radiography, and judges whether or not the stent 10 is deployed at a desired position of the stenosis 102. If the operator judges that the stent 10 is deployed while being misaligned with the stenosis 102, the operator accommodates the stent 10 into the device 12 again.

Figure 7B:
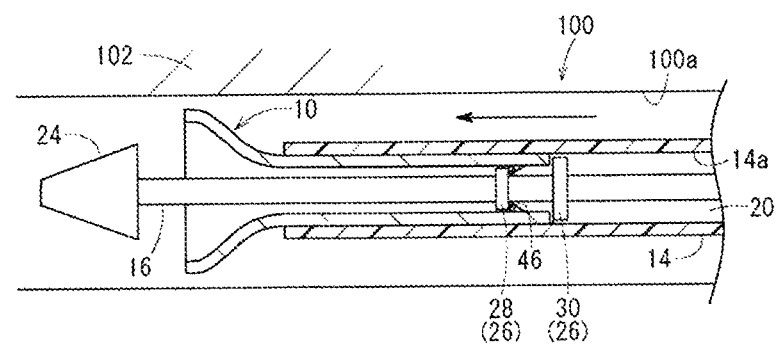
FIG. 7B is a second explanatory view for describing an operation when the stent in FIG. 1 expands.

As illustrated in FIG. 7B, when the stent 10 is accommodated again, the sheath 14 is moved forward relative to the shaft 16. In this manner, while the stent 10 is brought into the contract state, the stent 10 is accommodated in the accommodating lumen 20. At this time, pressure (forward moving force) acting from the inner wall 14*a* of the sheath 14 in the distal direction is applied to the stent 10. However, the anchor portion 46 comes into contact with the first ridge portion 28 so as to restrict the movement (displacement) of the stent 10.

In the contracted state of the stent 10, the anchor portion 46 protrudes so as to incline in the obliquely distal direction, and can exert strong resistance force against the first ridge portion 28. In accordance with an exemplary embodiment, when the stent 10 is intended to move in the distal direction, the anchor portion 46 locked by the first ridge portion 28 is operated so as to press the first ridge portion 28. Accordingly, the movement of the stent 10 in the distal direction can be firmly restricted. Therefore, the stent 10 can be smoothly accommodated into the sheath 14.

Figure 7C:
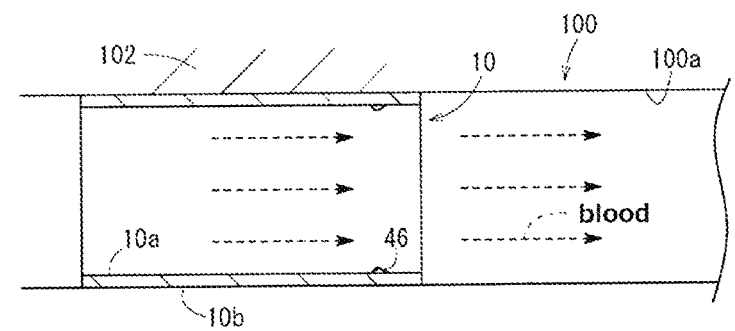
FIG. 7C is a third explanatory view for describing an operation when the stent in FIG. 1 expands.

As illustrated in FIG. 7C, the stent 10 is caused to normally indwell at a desired position inside the blood vessel 100, thereby enabling the stent 10 to satisfactorily expand and support the stenosis 102. In the indwelling state, the stent 10 is brought into the expanded state, and is located at a position where the anchor portion 46 is displaced to the inner surface 10*a* side of the stent 10. In accordance with an exemplary embodiment, the anchor portion 46 is almost aligned with the inner surface 10*a* of the stent 10. Accordingly, the stent 10 can help prevent the anchor portion 46 from being affected by the flow of the blood inside the blood vessel 100. Therefore, the stent 10 can be stably indwelled in the stenosis 102.

In addition, in the indwelling state of the stent 10, the anchor portion 46 applies elastic force so as to spread out the pair of proximal side extension portions 40*a* of the proximal turn-up portion 40 in the circumferential direction. Accordingly, the proximal portion of the stent 10 can have a greater expansion force than the conventional stent having no anchor portion 46, thereby improving force (locking force) of adhering to the vascular wall 100*a*. Therefore, an advantageous effect can be obtained in that the anchor portion 46 helps enable the stent 10 to more reliably indwell.

As described above, according to the stent 10 of the present embodiment, in the contracted state of the stent 10, the anchor portion 46 is separated from the inner surface 10*a* surrounding the cavity portion 34, and protrudes to the central axis O side. In this manner, the anchor portion 46 can be firmly locked by the first ridge portion 28 of the shaft 16 accommodated in the accommodating lumen 20 of the sheath 14. Therefore, the stent 10 is allowed to apply improved restriction force to the shaft 16, and thus the stent 10 can be prevented from following the forward movement of the sheath 14. As a result, an operator can accurately expand the stent 10 inside the blood vessel 100, and can cause the stent 10 to satisfactorily indwell at a desired position. In addition, in the stent 10 in the expanded state, the anchor portion 46 is displaced to the inner surface 10*a* side relative to the protruded position in the contracted state, thereby helping prevent the stent 10 from receiving an influence of the blood flowing inside the blood vessel 100. For example, in accordance with an exemplary embodiment, the stent 10 stably maintains the indwelling state inside the blood vessel 100.

In this case, the anchor portion 46 is configured to include the anchor strut 48 which is elastically deformable. Accordingly, in the contracted state of the stent 10, the anchor portion 46 easily protrudes to the central axis O side, and in the expanded state of the stent 10, the anchor portion 46 is smoothly and elastically restored together with the stent strut 32. Accordingly, the anchor portion 46 can be displaced to the inner surface 10*a* side of the stent 10.

In addition, the anchor portion 46 in the expanded state inclines in the protruded direction in the contracted state. Accordingly, when the stent 10 is switched from the expanded state to the contracted state (when elastically deformed), the anchor portion 46 can be caused to easily protrude to the central axis O side. Moreover, the anchor portion 46 has the valley portion 54 on the side opposite to the protruded direction. Accordingly, when elastically deformed, the anchor portion 46 can be operated so as to fold the valley portion 54, and can be caused to more reliably protrude (move forward and be displaced) to the central axis O side.

Furthermore, the length of the anchor strut 48 is shorter than the length of the stent strut 32. Accordingly, the stent 10 in the expanded state can move the anchor portion 46 so as to be sufficiently close to the inner surface 10*a* side, such that the possibility that the anchor portion 46 may receive an influence from the flow of the blood can be further minimized.

Without being limited to the above-described embodiment, the stent 10 according to the present disclosure can adopt various configurations, as a matter of course. Hereinafter, some modification examples according to the present disclosure will be described. In the following description, the same reference numerals are given to the same configuration elements or configuration elements having the same function as those of the stent 10 according to the present embodiment, and detailed description thereof will be omitted.

Figure 8A:
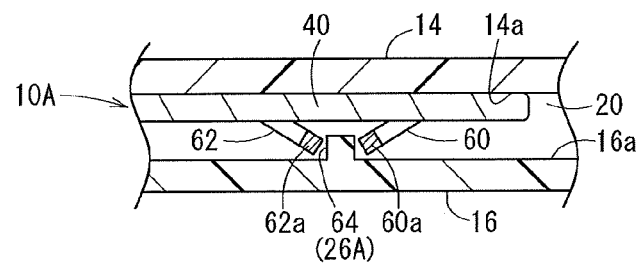
FIG. 8A is a partial side sectional view of a stent and a device for accommodating the stent according to a first modification example.
Figure 8B:
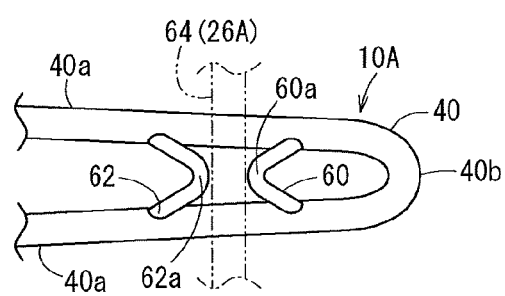
FIG. 8B is a partial plan view of only the stent in FIG. 8A.

As illustrated in FIGS. 8A and 8B, a stent 10A according to a first modification example has a configuration which includes a first anchor portion 60 protruded in the obliquely distal direction and a second anchor portion 62 protruded in the obliquely proximal direction in a state where the stent 10A is contracted and accommodated in the sheath 14. The first anchor portion 60 has the same configuration as that of the anchor portion 46 according to the present embodiment, and the second anchor portion 62 is disposed on the further distal side relative to the first anchor portion 60.

In a state of protruded from the inner surface 10*a* of the stent 10A, the second anchor portion 62 is formed in a shape substantially symmetrical to the first anchor portion 60 while one ridge portion 64 (stent locking portion 26A) formed to protrude on the shaft 16 serves as an axis of symmetry. In accordance with an exemplary embodiment, in a side sectional view as illustrated in FIG. 8A, the second anchor portion 62 inclines at an inclining angle, which is approximately the same as that of the first anchor portion 60. In a plan view as illustrated in FIG. 8B, the second anchor portion 62 shows a substantially V-shape which is the same as that of the first anchor portion 60.

The first and second anchor portions 60 and 62 are separated from each other by leaving a predetermined distance therebetween so that the ridge portion 64 of the shaft 16 can enter between the mutually disposed displacement peak portions 60*a* and 62*a*. Since the ridge portion 64 is present between the displacement peak portions 60*a* and 62*a* of the first and second anchor portions 60 and 62, both the first and second anchor portions 60 and 62 can be locked by the ridge portion 64.

In accordance with an exemplary embodiment, when the sheath 14 is moved rearward in order to expose the stent 10A, rearward moving force is applied to the stent 10A. However, in this case, the second anchor portion 62 is locked by the ridge portion 64. Accordingly, the stent 10 can be prevented from being displaced in the proximal direction. In accordance with an exemplary embodiment, when the sheath 14 is moved forward in order to accommodate the stent 10A again, forward moving force is applied to the stent 10A. However, in this case, the first anchor portion 60 is locked by the ridge portion 64. Accordingly, the stent 10A can be prevented from being displaced in the distal direction.

In this way, the stent 10A according to the first modification example includes the first and second anchor portions 60 and 62. Accordingly, the stent 10A can be prevented from moving in the axial direction (distal direction and proximal direction). Therefore, one ridge portion 64 may be disposed on the shaft 16 side. In addition, the first and second anchor portions 60 and 62 can more effectively assist the expansion of the proximal turn-up portion 40 of the stent 10A.

Figure 8C:
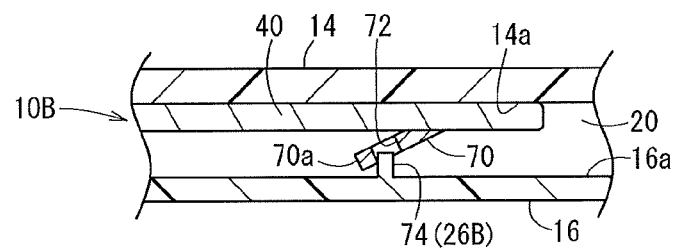
FIG. 8C is a partial side sectional view of a stent and a device for accommodating the stent according to a second modification example.
Figure 8D:
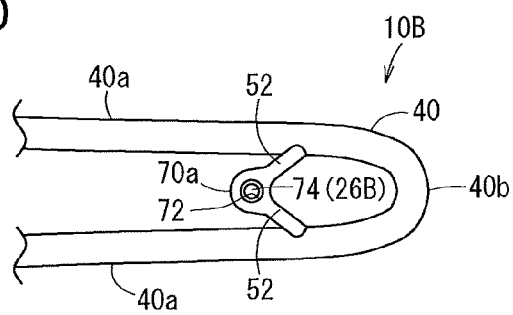
FIG. 8D is a partial plan view of the stent in FIG. 8C.

As illustrated in FIGS. 8C and 8D, a stent 10B according to a second modification example has a configuration in which a hole portion 72 is formed in an anchor portion 70 and a pin 74 (stent locking portion 26B) disposed on the shaft 16 can be inserted into the hole portion 72. In accordance with an exemplary embodiment, a displacement peak portion 70a of the anchor portion 70 is formed in a flat plate shape, and the hole portion 72 is formed in the central portion of the displacement peak portion 70a.

In a contracted state of the stent 10B, the displacement peak portion 70a is supported by the pair of bridge portions 52, and protrudes to the central axis O side relative to the inner surface 10a of the stent 10B. In response to the protrusion, the pin 74 is inserted into the hole portion 72.

Therefore, even if rearward moving force is applied to the stent 10B from the sheath 14, the displacement peak portion 70a (hole portion 72) and the pin 74 are locked. Accordingly, the stent 10B can be prevented from being displaced in the proximal direction. Similarly, even if forward moving force is applied to the stent 10B from the sheath 14, the displacement peak portion 70a (hole portion 72) and the pin 74 are locked. Accordingly, the stent 10B can be prevented from being displaced in the distal direction.

Figure 9A:
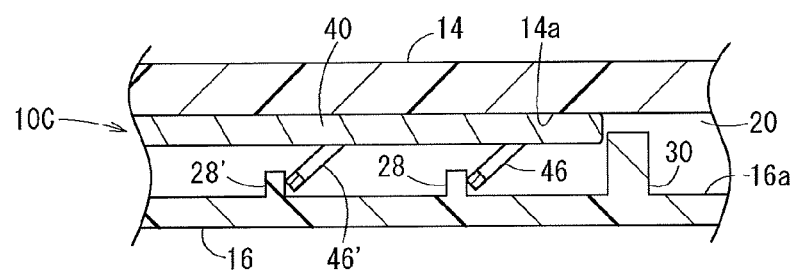
FIG. 9A is a partial side sectional view of a stent and a device for accommodating the stent according to a third modification example.

As illustrated in FIG. 9A, a stent 10C according to a third modification example has a configuration in which the anchor portion 46 is disposed at two locations in the axial direction of the proximal turn-up portion 40. These two anchor portions 46 and 46' protrude in the obliquely distal direction in the contracted state, and respectively come into contact with the first ridge portion 28 and a third ridge portion 28' which are disposed on the shaft 16. In this manner, the stent 10C can more firmly be prevented from being displaced.

In short, without being limited to one, the number of anchor portions in the axial direction of the stent may be two or more. In addition, a position for forming the anchor portion in the axial direction of the stent is not particularly limited. For example, the anchor portion may be formed on the distal side or in a body portion of the stent.

Figure 9B:
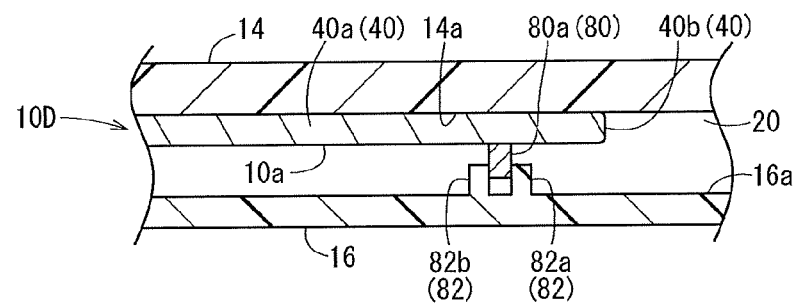
FIG. 9B is a partial side sectional view of a stent and a device for accommodating the stent according to a fourth modification example.

As illustrated in FIG. 9B, a stent 10D according to a fourth modification example is configured so that a displacement direction of an anchor portion 80 is a direction which is orthogonal to the inner surface 10a of the stent 10D. In accordance with an exemplary embodiment, when the pair of proximal side extension portions 40a are moved close to each other by the contracted stent 10D, a pair of bridge portions 80a of the anchor portion 80 protrude (move forward) so as to be orthogonal to the central axis O. In contrast, a stent locking portion 82 (first ridge portion 82a and second ridge portion 82b) is disposed on the outer wall 16a of the shaft 16, and the anchor portion 80 enters between the first and second ridge portions 82a and 82b.

In this manner, even if rearward moving force is applied to the stent 10D from the sheath 14, the anchor portion 80 and the first ridge portion 82a are locked. Accordingly, the stent 10D can be prevented from being displaced in the proximal direction. Similarly, even if forward moving force is applied to the stent 10D from the sheath 14, the anchor portion 80 and the second ridge portion 82b can be locked. Accordingly, the stent 10D can be prevented from being displaced in the distal direction.

In addition, as another modification example of the anchor portion, the following configuration may be adopted as a matter of course. When it is not considered to accommodate the stent again, on the contrary to the configuration in which an anchor portion protrudes in the obliquely distal direction as the anchor portion 46 according to the present embodiment, an anchor portion which protrudes only in the obliquely proximal direction may be disposed so as to prevent the stent 10 from following the rearward movement of the sheath 14.

Furthermore, the present disclosure may adopt not only a configuration in which flexibility is provided by forming the anchor strut 48 so as to be thinner than the stent strut 32 as in the stent 10 according to the present embodiment, but also a configuration in which the anchor portion is elastically and smoothly deformed by forming the anchor strut 48 using a material having lower modulus of elasticity than the stent strut 32.

Furthermore, without being limited to the structure (ridge portion) which protrudes relative to the outer wall 16a of the shaft 16, for example, the stent locking portion 26 formed on the shaft 16 may adopt a configuration in which a groove is formed on the outer wall 16a of the shaft 16 so that the anchor portion 46 enters the groove.

Hitherto, the preferred embodiments according to the present invention have been described. However, without being limited to the above-described embodiments, the present invention can be improved or modified in various ways within the scope not departing from the gist of the present invention, as a matter of course.

The detailed description above describes a stent. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A stent which is formed in a cylindrical shape and has a cavity portion, wherein the stent is freely switched between an expanded state and a contracted state where the stent contracts to a central axis side from the expanded state, the stent comprising:
    a movable protruded portion which is protruded to the central axis side relative to an inner surface surrounding the cavity portion in the contracted state, and which is displaced to the inner surface side in the expanded state relative to a protruded position in the contracted state; and
    wherein the stent in the contracted state is accommodated in a lumen of a sheath which can be delivered into a living body lumen, and is arranged so as to surround an inner structure body which is inserted into the lumen and wherein the movable protruded portion inclines in a direction in which the sheath is movable relative to the inner structure body, and
    a peak portion of the movable protruded portion protruded inward most relative to the inner surface can be locked by a locking portion formed on an outer peripheral surface of the inner structure body.

2. The stent according to claim 1,
    wherein the stent includes an element wire configuring a stent body and an element wire configuring the movable protruded portion, and wherein the element wire configuring the movable protruded portion is formed of a shape memory alloy.

3. The stent according to claim 2,
wherein the element wire configuring the movable protruded portion is more flexible than the element wire configuring the stent body.

4. The stent according to claim 2,
wherein the element wire configuring the stent body has a pair of extension portions which extend toward an axial end portion of the stent and a turn-up peak portion which is curvedly connected to the pair of extension portions, and
wherein the element wire configuring the movable protruded portion in the expanded state is connected to the pair of extension portions so as to incline in a protruded direction in the contracted state.

5. The stent according to claim 4,
wherein the element wire configuring the movable protruded portion in the expanded state has a valley portion on a side opposite to the protruded direction.

6. The stent according to claim 4,
wherein both end portions of the movable protruded portion are respectively connected to two connection points on the pair of extension portion, and
wherein a length extending along the element wire configuring the movable protruded portion between the two connection points is shorter than a length extending along the element wire configuring the stent body between the two connection points.

7. The stent according to claim 1,
wherein the stent includes an element wire configuring a stent body and an element wire configuring the movable protruded portion, and
wherein the element wire configuring the movable protruded portion is formed of a shape memory alloy.

8. The stent according to claim 7,
wherein the element wire configuring the movable protruded portion is more flexible than the element wire configuring the stent body.

9. The stent according to claim 7,
wherein the element wire configuring the stent body has a pair of extension portions which extend toward an axial end portion of the stent and a turn-up peak portion which is curvedly connected to the pair of extension portions, and
wherein the element wire configuring the movable protruded portion in the expanded state is connected to the pair of extension portions so as to incline in a protruded direction in the contracted state.

10. The stent according to claim 9,
wherein the element wire configuring the movable protruded portion in the expanded state has a valley portion on a side opposite to the protruded direction.

11. The stent according to claim 9,
wherein both end portions of the movable protruded portion are respectively connected to two connection points on the pair of extension portion, and
wherein a length extending along the element wire configuring the movable protruded portion between the two connection points is shorter than a length extending along the element wire configuring the stent body between the two connection points.

12. The stent according to claim 1, wherein the movable protruded portion is V-shaped in the contracted state, and the stent includes at least three movable protruded portions arranged at equal intervals in a circumferential direction of the stent.

13. The stent according to claim 1, wherein the movable protruded portion comprises at least one first anchor portion protruded in an obliquely distal direction and at least one second anchor portion protruded in an obliquely proximal direction in the state where the stent is contracted and accommodated in the sheath.

14. A stent comprising:
a cylindrical shape having a cavity portion, the stent being configured to be freely switched between an expanded state and a contracted state where the stent contracts to a central axis side from the expanded state;
a movable protruded portion which is protruded to the central axis side relative to an inner surface surrounding the cavity portion in the contracted state, and which is displaced to the inner surface side in the expanded state relative to a protruded position in the contracted state; and
wherein the stent in the contracted state is accommodated in a lumen of a sheath which can be delivered into a living body lumen, and is arranged so as to surround an inner structure body which is inserted into the lumen, and
wherein the movable protruded portion inclines in a direction in which the sheath is movable relative to the inner structure body, and a peak portion of the movable protruded portion protruded inward most relative to the inner surface can be locked by a locking portion formed on an outer peripheral surface of the inner structure body.

15. The stent according to claim 14, comprising:
an element wire configuring a stent body and an element wire configuring the movable protruded portion, and
wherein the element wire configuring the movable protruded portion is formed of a shape memory alloy.

16. The stent according to claim 15, wherein the element wire configuring the movable protruded portion is more flexible than the element wire configuring the stent body.

17. The stent according to claim 15, wherein
the element wire configuring the stent body has a pair of extension portions which extend toward an axial end portion of the stent and a turn-up peak portion which is curvedly connected to the pair of extension portions; and
wherein the element wire configuring the movable protruded portion in the expanded state is connected to the pair of extension portions so as to incline in a protruded direction in the contracted state.

18. The stent according to claim 17,
wherein the element wire configuring the movable protruded portion in the expanded state has a valley portion on a side opposite to the protruded direction.

19. The stent according to claim 17,
wherein both end portions of the movable protruded portion are respectively connected to two connection points on the pair of extension portion, and
wherein a length extending along the element wire configuring the movable protruded portion between the two connection points is shorter than a length extending along the element wire configuring the stent body between the two connection points.

\* \* \* \* \*